United States Patent [19]

Swirski, Jr.

[11] Patent Number: 5,019,999
[45] Date of Patent: May 28, 1991

[54] IMMUNOANALYSIS METHOD FOR DISCRIMINATING BETWEEN ANTIGEN EXCESS AND ANTIBODY EXCESS CONDITIONS

[75] Inventor: Chester Swirski, Jr., Hopewell Junction, N.Y.

[73] Assignee: Technicon Instruments Corporation, Tarrytown, N.Y.

[21] Appl. No.: 252,420

[22] Filed: Sep. 30, 1988

[51] Int. Cl.$^5$ .................. G01N 31/00; G06F 15/20
[52] U.S. Cl. .................. 364/497; 364/413.1; 356/339; 356/341; 436/150; 436/805
[58] Field of Search .......... 364/497, 413.1, 413.11; 356/338, 339, 341, 39; 436/805, 149, 150

[56] References Cited

U.S. PATENT DOCUMENTS

| | | | |
|---|---|---|---|
| 4,157,871 | 6/1979 | Anderson et al. | 356/341 |
| 4,204,837 | 5/1980 | Sternberg et al. | 356/341 |
| 4,368,509 | 1/1983 | Li | 364/497 |
| 4,460,967 | 7/1984 | Krull et al. | 364/497 |
| 4,468,742 | 8/1984 | Jenden et al. | 364/497 |
| 4,631,687 | 12/1986 | Kowalski et al. | 364/497 |

*Primary Examiner*—Parshotam S. Lall
*Assistant Examiner*—Brian M. Mattson

*Attorney, Agent, or Firm*—Vorys, Sater, Seymour & Pease

[57] ABSTRACT

A method of immunoassay for analyzing a bodily fluid for the presence of an analyte relies on observing substantially the entire course of a precipitin reaction from initiation to substantial completion of the precipitation, defining a mathematical function which represents the amount of precipitation versus time and contains constants which can be adjusted so that the function matches the observed precipitation versus time curve, and fitting the observed data to the mathematical function by adjusting the constants so that the mathematical function matches the observed precipitation versus time curve as closely as possible. Values for the maximum rate of precipitation and for the time interval from initiation of the precipitation to the time of maximum rate of precipitation are calculated from the mathematical function. A reference curve is generated using standard containing known concentrations of analyte according to conventional analytical procedures. The values so calculated for the parameters of the precipitation can then be used to determine whether a given sample presents a condition of antigen (analyte) excess and must be discarded or a condition of antibody excess which can be used in conjunction with the reference curve to report a valid concentration of analyte.

4 Claims, 3 Drawing Sheets

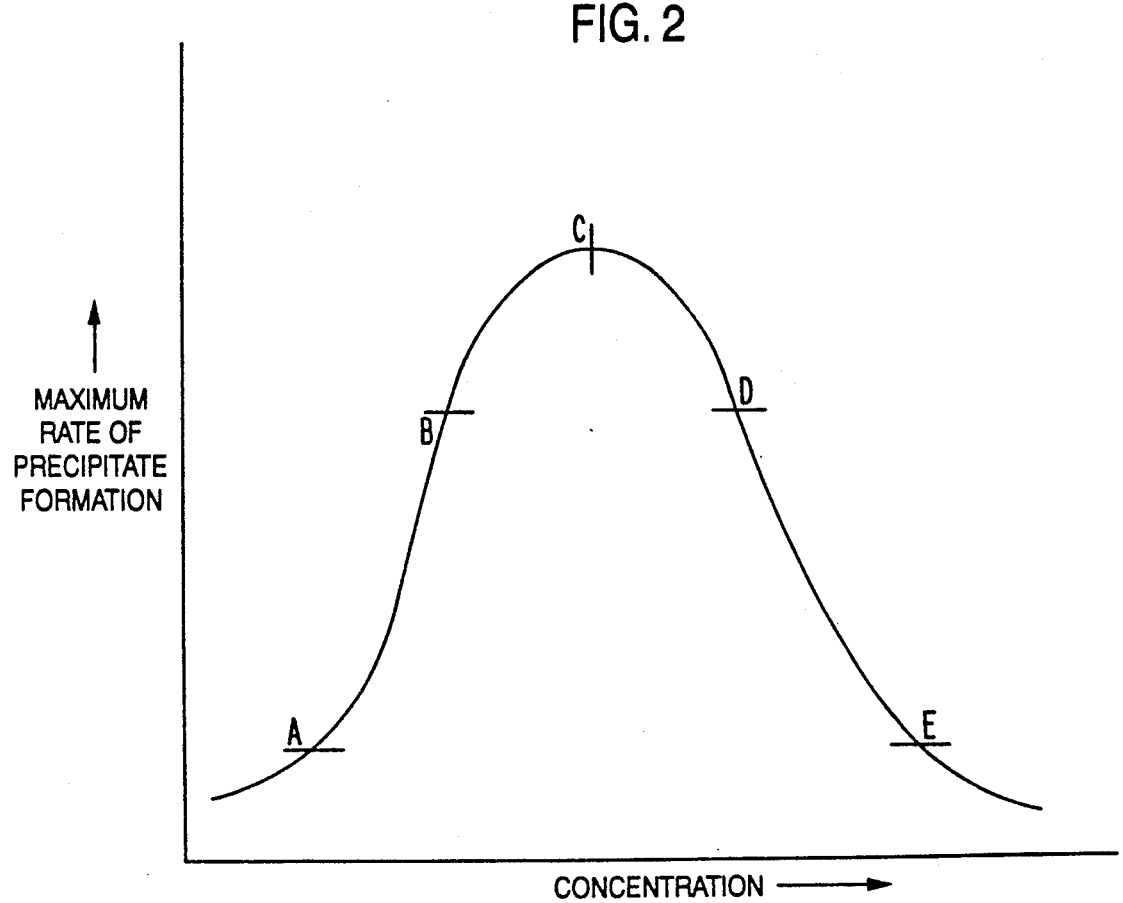

IMMUNOANALYSIS METHOD FOR DISCRIMINATING BETWEEN ANTIGEN EXCESS AND ANTIBODY EXCESS CONDITIONS

BACKGROUND OF THE INVENTION

1. Field of the Invention

This invention relates to methods of immunoanalysis and more particularly to methods of immunoanalysis using precipitates of immunocomplexes.

2. Description of the Prior Art

Immunoanalysis is used extensively in biochemistry and clinical chemistry to determine the concentration of proteins and other antigenic materials in biological fluids, such as blood plasma. Immunoanalysis relies on the ability of an antibody, raised against an antigen, to combine with the antigen to form an immunocomplex. Conventionally, a known amount of either the antigen or antibody is reacted with an unknown amount of the complementary immunoreagent, and some property of the resulting immunocomplex is measured in order to determine the amount of the unknown component which was present. The immunocomplex formed by the interaction of an antigen and antibody is often insoluble in the aqueous media in which the immunoanalysis is conducted. This property of the immunocomplex forms the basis of immunoanalysis using the "precipitin" reaction which has been used extensively in immunoanalysis. A detailed discussion of the precipitin reaction and its use in immunoanalysis is found in Tietz, N. W., Ed., Textbook of Clinical Chemistry, W. B. Saunders Co. Philadelphia, 1986, pp. 212-215.

In a properly conducted precipitin reaction the total amount of precipitate of immunocomplex formed is proportional to the amount of immunoreagent present over a range of concentration of immunoreagent. Accordingly, when the concentrations are within this suitable range the precipitate can be merely collected and weighed. However, this simple form of immunoassay using the precipitin reaction has a number of drawbacks. The precipitate of immunocomplex may be difficult to collect and weigh. More important, the precipitate will not form or will redissolve if one of the immunoreagents is present in great excess. Even if the proportions of the reagents are within a range suitable for quantitative immunoanalysis, the formation of the precipitate may be slow, and accordingly, it may be difficult to tell whether the reaction is quantitatively complete. In addition, simple gravimetric analysis is not amenable to automated analytical methods which are favored for clinical immunoassays today.

Accordingly, immunoanalytical methods using the precipitin reaction have resorted to other methods of measuring the amount of immunocomplex precipitate present in an analytical sample. In particular, methods have been developed which use the light-scattering properties of the immunocomplex precipitate to determine the amount of precipitate formed in the immunoreaction. However, the precipitin reaction still suffers from the problems associated with slow attainment of equilibrium, limited range of quantitative relation between precipitate formed and concentration of immunoreagents, and the formation of smaller amounts of precipitate if one of the reagents, e.g., the antigen, is in excess. Since it is more common to analyze for an antigen by reacting a sample containing an unknown amount of antigen with a known quantity of antibody, this problem is usually described as the antigen excess problem.

A nephelometric apparatus for performing immunoanalysis using the precipitin reaction wherein the amount of precipitate formed is measured by its light scattering property, together with a method of immunoanalysis using nephelometry to determine the amount of precipitate present in the sample at a given time, is disclosed in Anderson, U.S. Pat. No. 4,157,871, the entire specification of which is incorporated herein by reference. In Anderson's apparatus the electrical signal representing the intensity of scattered light is differentiated to derive a reaction rate, and the rate signal is again differentiated to derive a peak reaction rate which is found to be characteristic of the concentration of analytes in the sample solution. Anderson discloses that the peak rate of formation of the precipitate may be used in place of the total amount of precipitate formed as a measure of the amount of antigen in the sample. Anderson also discloses methods of manipulating the data derived from the scatter versus time signal to permit a determination of the condition of the sample and determine whether antigen is present in excess amount. However, Anderson teaches only measuring the scatter signal essentially up to the time at which it attains its peak rate. Anderson does not teach following the formation of the precipitate at times after it reaches its peak rate of formation.

Another method of determining whether the sample in a nephelometric precipitin immunoassay is in an antigen excess or antibody excess condition is disclosed by Sternberg, U.S. Pat. No. 4,204,837, the entire specification of which is incorporated herein by reference. Sternberg uses the peak rate of precipitate formation as well as the time interval from the beginning of the reaction to the time of peak rate to determine whether an additional amount of antigen or antibody should be added to the test sample to determine unambiguously whether the sample is in antigen excess or antibody excess.

However, the prior art does not teach monitoring the amount of precipitate formed beyond the achievement of the peak rate or for a fixed time interval which may coincide with the entire precipitin reaction from initiation to end point. Accordingly, useful data which can be used to derive a more accurate value for the antigen concentration and for determining whether a given sample is in a condition of antigen excess has been neglected.

Hence, a need has continued to exist for a method of immunoanalysis using the precipitin reaction which uses the information available from observing the course of the formation of the immunocomplex precipitate in order to determine the concentration of antigen and to determine whether a given sample is in a condition of antigen excess.

SUMMARY OF THE INVENTION

This goal has now been achieved by a method of immunoassay for analyzing a bodily fluid for the presence of an analyte which relies on observing the course of a precipitin reaction from initiation to substantial completion of the precipitation, defining a mathematical function which represents the amount of precipitation versus time and contains constants which can be adjusted so that the function matches the observed precipitation versus time curve, and fitting the observed data to the mathematical function by adjusting the constants so that the mathematical function matches the observed precipitation versus time curve as closely as possible. Values for the maximum rate of precipitation and for the time interval from initiation of the precipitation to the time of maximum rate of precipitation are calculated from the mathematical function. A reference curve is generated using standards containing known concentrations of analyte according to conventional analytical procedures. The values so calculated for the parameters of the precipitation can then be used in the method of this invention to determine whether a given sample presents a condition of antigen (analyte) excess and reporting the existence of this condition or a condition of antibody excess which can be used in conjunction with the reference curve to report a valid concentration of analyte.

The method then comprises the steps of:

1) generating a reference curve by:
   a) preparing a series of standard samples of fluid containing varied known amounts of an analyte;
   b) initiating reaction of each of the standard samples with a predetermined amount of a complementary immunoreagent capable of forming an insoluble complex by reaction with the analyte to form a reaction mixture, whereby a precipitate of an immunocomplex begins to form in the reaction mixture and the formation of the precipitate continues over a period of time;
   c) for each of the reaction mixtures, detecting a physical property of the reaction mixture which is quantitatively proportional to the amount of the precipitate present in the reaction mixture at any time and generating a signal proportional to the magnitude of the physical property;
   d) recording the value of the signal at various times within the period of time, whereby an assembly of data comprising the numerical values of the signals and the times at which the values were recorded, is collected, representing the amount of the precipitate formed as a function of time;
   e) defining a mathematical function which represents the amount of the precipitate formed as a function of time in the reaction mixture, the function having the form:

$$S = \frac{M \times t^m}{(K + t^n)} + B$$

wherein S represents the amount of the precipitate, t represents time, m and n are constants between 1 and 3 preselected to provide an assumed precipitate versus time curve, and M, K and B are constants derived by fitting the data recorded in step 1) d) to the mathematical function;
   f) mathematically fitting the data recorded in step 1) d) to the function defined in step 1) e), whereby numerical values are determined for constants M, K and B and the constants in the function of step 1) d) are replaced by the numerical values;
   g) determining the maximum rate of formation of the precipitate for each reaction mixture by calculating the maximum rate of change of the function of step 1) e) from the constants M, K and B; and
   h) plotting the maximum rate for each of the samples against the concentration of the analyte in the reaction mixture, whereby a reference curve is generated representing the maximum rate of formation of the precipitate which is characteristic of each concentration of the analyte, the reference curve having the property that the maximum rate of formation of precipitate:
      has a maximum value defining an equivalence point for a concentration of the analyte approximately equivalent to the predetermined amount of complementary immunoreagent,
      has a value lower than the maximum value for a concentration of the analyte less than the equivalence point, and
      has a value lower than the maximum value for a concentration of analyte in excess of the equivalence point;
   i) defining a point A representing a concentration below the equivalence point on the reference curve which corresponds to the minimum concentration of the analyte to be reported from the reference curve;
   j) defining a point B representing a concentration below the equivalence point on the reference curve which corresponds to the maximum concentration of the analyte to be reported from the reference curve;
   k) defining a point X representing a concentration below the equivalence point on the reference curve between point A and point B;

2) initiating reaction of a fluid sample which is an aliquot of a body fluid sample containing an unknown quantity of the analyte with the predetermined amount of the complementary immunoreagent to form a test sample, whereby a precipitate of the immunocomplex begins to form in the test sample and the formation of the precipitate continues over a period of time;

3) calculating the maximum rate of formation of the precipitate formed in step 2) by:
   a) detecting in the test sample the physical property of step 1) c) which is quantitatively proportional to the amount of the precipitate present in the reaction mixture at any time and generating a signal proportional to the magnitude of the physical property;
   b) recording the values of the signal of step 3) a) at various times within the period of time of step 2), whereby an assembly of data, comprising the numerical values of the signal of step 3) a) and the times at which the values were recorded, is collected representing the amount of the precipitate formed in step 2) as a function of time;
   c) mathematically fitting the data recorded in step 3) b) to the function defined in step 1) e), whereby numerical values are determined for constants M, K and B and the constants in the function of step 1) e) are replaced by the numerical values;
   d) determining the maximum rate of formation of the precipitate formed in step 2) by calculating the maximum rate of change of the function of step 1) e) from the constants M, K and B;

4) identifying the maximum rate of formation of the precipitate calculated in step 3) d) as a first maximum rate and if the first maximum rate is less than that associated with point A,
   rejecting the sample as too dilute for accurate measurement and repeating steps 2) and 3) using a less dilute fluid sample;

5) identifying the maximum rate of formation of the precipitate calculated in step 4) using the less dilute fluid sample as a second maximum rate, and if the second maximum rate is greater than that associated with point A, and less than that associated with point B, reading the concentration from the reference curve at the point corresponding to the second calculated maximum rate of formation and reporting the concentration of the analyte in the test sample of step 4;

6) if the second maximum rate of formation is less than that associated with point A,
   adding to the test sample of step 4) a solution containing a predetermined amount of the analyte and again calculating the maximum rate of formation of precipitate of the immunocomplex by following the procedure of steps 3) a) through 3) d);

7) identifying the maximum rate of formation of the precipitate calculated in step 6) as a third maximum rate and if the third maximum rate is greater than that associated with point A,
   reporting the less dilute sample as containing a concentration of analyte which is less than the concentration associated with point A;

8) if the third maximum rate is less than that associated with point A,
   reporting the test sample as presenting a condition of antigen excess;

9) if the first maximum rate is greater than that associated with point A and greater than that associated with point B,
   reporting the test sample as containing an amount of analyte too great for accurate measurement;

10) if the first maximum rate of formation is greater than that associated with point A and less than that associated with point B,
    calculating the time interval between the reaction initiation of step 2) and the time the reaction reaches the first maximum rate;

11) if the time interval calculated in step 10) is greater than a predetermined interval,
    reporting the test sample as presenting a condition of antigen excess;

12) if the time interval calculated in step 10) is less than the predetermined interval of step 11),
    determining a second precipitate versus time function from the data recorded in step 3) b) by repeating the procedure of step 3) c) through step 3) d) using a value t-D in place of t, where D is a predetermined time, and all data points collected at less than time D are omitted from the curve fitting procedure, and calculating from the second precipitate versus time function a fourth maximum reaction rate;

13) if the fourth maximum reaction rate is greater than a predetermined value T,
    reporting the test sample as presenting a condition of antigen excess;

14) if the fourth maximum reaction rate is less than or equal to the predetermined value T,
    adding a second aliquot of the sample to the reaction and again repeating the procedure of steps 3) a) through 3) d) to calculate therefrom a fifth maximum reaction rate;

15) if the first maximum reaction rate is greater than that associated with point X and the first maximum reaction rate multiplied by a predetermined factor Z is less than or equal to the fifth maximum reaction rate,
    reporting the test sample as presenting a condition of antigen excess;

16) if the first maximum maximum reaction rate is greater than that associated with point X and the first maximum reaction rate multiplied by a predetermined factor Z is greater than the fifth maximum reaction rate,
    reporting the concentration of analyte in the test sample by reading the value corresponding to the first maximum reaction rate from the reference curve between points A and B;

17) if the first maximum reaction rate is less than or equal to that associated with point X and the first maximum reaction rate multiplied by a predetermined factor Y is less than or equal to the fifth maximum reaction rate of,
    reporting the test sample as presenting a condition of antigen excess;

18) if the first maximum reaction rate is less than or equal to that associated with point X and the first maximum reaction rate multiplied by a predetermined factor Y is greater than the fifth maximum reaction rate,
    reporting the concentration of analyte in the test sample by reading the value corresponding to the first maximum reaction rate from the reference curve between points A and B.

Accordingly, it is an object of the invention to provide a method of immunoanalysis.

A further object is to provide a method of immunoanalysis using the rate of formation of an immunocomplex precipitate as the parameter characterizing the concentration of the analyte.

A further object is to provide a method of immunoanalysis capable of detecting a condition of antigen excess in the analytical sample which is observed.

Other objects of the invention will become apparent from the description of the invention which follows.

BRIEF DESCRIPTION OF THE DRAWINGS

The invention will be better understood by reference to the accompanying drawings wherein:

FIG. 2 shows a reference curve plotting the maximum rate of formation of precipitate in a precipitin reaction against the concentration of antigen when the amount of antibody in the observation sample is constant.

DETAILED DESCRIPTION OF THE INVENTION AND PREFERRED EMBODIMENTS

The method of the invention makes use of the fact that the rate of formation of the precipitate of immunocomplex in a precipitin reaction is correlated with the amount of reagents present.

Figure 1A:
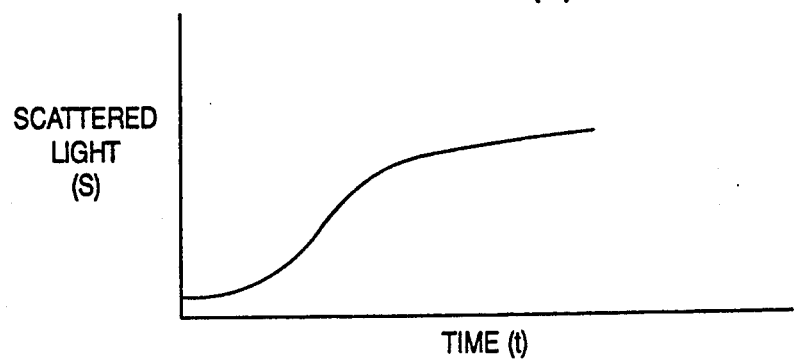
FIG. 1(a) is a plot of the light scattered from an observation sample in which an insoluble precipitate of an immunocomplex is forming as a function of time, for the condition in which the amount of antigen present is less than the amount equivalent to the amount of antibody in the sample.
Figure 1B:
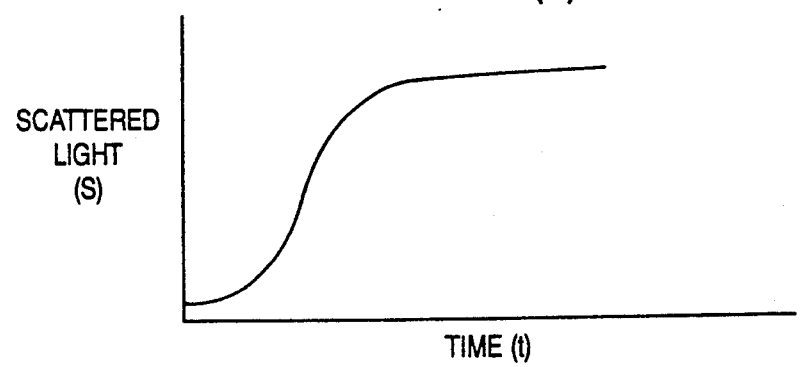
FIG. 1(b) is a plot of the light scattered from an observation sample in which an insoluble precipitate of an immunocomplex is forming as a function of time, for the condition in which the amount of antigen present is approximately equivalent to the amount of antibody in the sample.
Figure 1C:
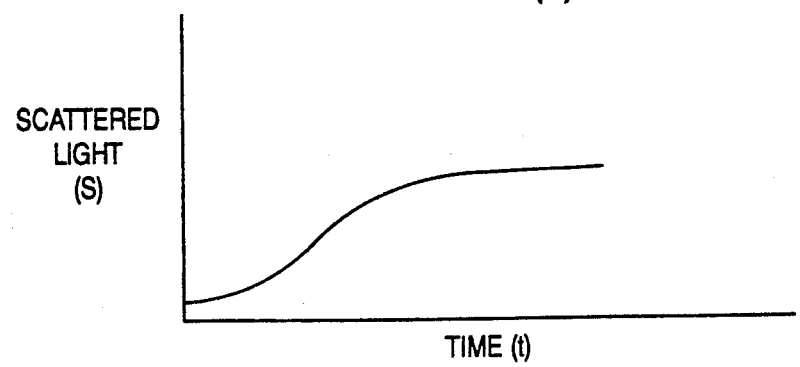
FIG. 1(c) is a plot of the light scattered from an observation sample in which an insoluble precipitate of an immunocomplex is forming as a function of time, for the condition in which the amount of antigen present is greater than the amount equivalent to the amount of antibody in the sample.

Referring now to FIG. 1, the drawing represents the time course of the precipitin reaction, as followed by light scattering, for three conditions of the antigen concentration. In each case the amount of antibody is constant, but the amount of antigen is varied to illustrate the effect of differing ratios of antigen to antibody on the amount of precipitate formed and the rate at which it is formed.

FIG. 1 (a) shows the condition of antibody excess. The rate of precipitation is slow initially, increases to a maximum rate, then decreases as the precipitation approaches completion. The maximum scatter attained is proportional to the amount of antigen present; however the final level of scattering is attained slowly, and it is difficult to determine when the end of the precipitation has been reached. Accordingly, using the maximum scatter as a measure of the total concentration of antigen is subject to certain inaccuracies.

FIG. 1 (b) shows the condition of equivalence between antigen and antibody. The general shape of the curve is similar to that of FIG. 1 (a), but the total scatter at the completion of the precipitation is greater. The precipitation reaction also proceeds faster than when the amount of antigen is less than the equivalent amount.

FIG. 1 (c) shows the condition of antigen excess. The general shape of the scatter versus time curve is similar to that of FIGS. 1 (a) and 1 (b). However, the maximum scatter attained by the sample is less than that for the condition of equivalence, and the maximum rate of formation of the precipitate is also correspondingly less.

If the maximum rate of precipitation is plotted against the concentration of antigen for a series of reactions wherein the amount of antibody is held constant and the amount of antigen is varied, a reference curve of the form shown in FIG. 2 is obtained. When the concentration of antigen is very low, the maximum rate of precipitation is correspondingly small. When the concentration of antigen is greater, the rate of precipitation is also greater up to the point at which the amount of antigen is equivalent to the fixed amount of antibody. At higher concentrations of antigen, the antigen excess region, the maximum rate of precipitation decreases. In this way, the reference curve of maximum rate versus concentration is similar to the curve of maximum amount of precipitate formed versus concentration, as shown, for example in the book by Tietz referred to above. However, a nephelometric determination using the maximum rate of formation of precipitate is not subject to the same uncertaincies as the determination of the maximum amount of precipitate formed.

In using the reference curve of FIG. 2 to determine the concentration of antigen in an analytical sample, it is preferred to read the concentration from the curve in the antibody excess region between the points indicated by A and B. When the concentration of antigen in the sample is less than that corresponding to point A, the maximum rate does not change very rapidly with changing concentration. Accordingly, it is difficult to read the concentration accurately from the curve, and maximum rates in this region are not used for analysis. In the equivalence region of the curve, from point B through the equivalence point C to point D, which corresponds to the same concentration as point B, the curve also changes less rapidly with changing concentration than it does between points A and B, and also begins to decrease with increasing antigen concentration. Again, readings in the equivalence region of the reference curve are not used in analysis. In the region of antigen excess, to the right of point D, the rate of precipitation continues to decrease with increasing concentration of antigen. In the portion of the curve between D and E, which lies between the concentrations corresponding to points B and A, respectively, a given maximum rate of precipitate formation corresponds to two possible values of the antigen concentration, one in the antibody excess region and one in the antigen excess region. Accordingly, for maximum rate readings between points A' and B', the data are ambiguous, and a determination must be made as to whether the data represent a sample in the antibody excess region of the reference curve or the antigen excess region of the curve. Finally, in the region of the curve to the right of point E, the maximum rate readings are too small to be used for analysis. However, it is desirable to determine whether the maximum rate readings in this region correspond to a condition of very little antigen (concentration less than point A) or of extreme antigen excess (concentration greater than point E), in order to decide whether it is possible to conduct a successful analysis by using more or less dilute samples to bring the measured maximum rate of precipitate formation into the useful region of the reference curve.

The determination of the maximum rate of precipitation has been conducted by differentiation of the scatter signal and measuring the peak rate of change of the scatter signal, as taught by Anderson, U.S. Pat. No. 4,157,871. This method effectively follows the precipitation reaction up to the point at which the rate of precipitation begins to decrease.

The method of this invention uses the scatter versus time curve beyond the point at which the maximum rate is achieved or for a fixed time interval which may coincide with the entire reaction to derive a maximum rate which may be used to determine the concentration of antigen. According to the method of this invention, an analytical function is selected of the form:

$$S = \frac{M \times t^m}{(K + t^n)} + B \tag{1}$$

wherein S represents the amount of the precipitate, t represents time, m and n are exponents of t selected to provide the best shape of the curve to fit the scatter versus time curve, and M, K and B are constants.

As will be recognized by those skilled in the art, an equation of the form of Formula (1) yields a curve which approximates the generally S-shaped curve of the scatter versus time function exhibited by the precipitin reaction. The representation of the curve can be optimized by selecting suitable values for the exponents m and n. However, satisfactory results are obtained when m and n are each set equal to 2. The formula used in the preferred method of the invention therefore becomes:

$$S = \frac{M \times t^2}{(K + t^2)} + B \quad (2)$$

wherein S represents the amount of the precipitate, t represents time, and M, K and B are constants.

In order to derive a reference curve for a particular precipitin reaction, a series of standards is prepared comprising varied concentrations of the antigen which is the analyte. Each standard is mixed with a fixed predetermined amount of an antibody, usually in aqueous solution, to form a reaction mixture and initiate the formation of a precipitate of immunocomplex. The amount of precipitate formed as a function of time is determined by monitoring some observable property of the reaction mixture which is proportional to the amount of precipitate formed. Preferably, the property is the amount of light scattered by the fine particles of precipitate suspended in the reaction mixture. A set of data is recorded comprising the intensity of the scattered light at selected times after the initiation of the reaction. These values represent S and t, respectively, in equation (2). The data are preferably recorded over a period of time extending until the precipitation is substantially complete. In this way, data points may be taken over the entire course of reaction and used in deriving values for the maximum rate and other parameters used in the method of the invention. This assures a value more representative of the precipitin reaction being analyzed than prior art methods which derive a peak rate based only on a few data points taken near the region of maximum rate of formation of precipitate.

By fitting the function represented by equation (2) to the set of data recorded during the course of the precipitin reaction, values can be assigned to the constants M, K and B. This curve fitting can be carried out by established mathematical procedures such as by the method of non-linear least squares. The curve fitting can conveniently be accomplished automatically by the use of a suitably programmed digital computer. The curve fitting step which generates values for the constants M, K, and B is entirely conventional and forms no part of the invention.

Once a curve having the form of equation (2) has been derived, the maximum rate of formation and the time interval from the initiation of the reaction to the time at which the maximum rate occurs can be calculated from equation (2) by the following formulas:

$$\text{Maximum rate} = \frac{0.65 \times M}{K^{0.5}} \quad (3)$$

$$\text{Time to maximum rate} = \left[\frac{K}{3}\right]^{0.5} \quad (4)$$

The reference curve is then prepared by plotting the calculated reaction rate for each reaction mixture against the known concentration of antigen in that mixture. The resulting reference curve will resemble the curve illustrated in FIG. 2. It may be seen from FIG. 2 that at values of the concentration less than that corresponding to point A, the maximum rate of precipitation changes rather slowly with the concentration. Hence, samples found to be in this region of the curve are discarded, and the reaction is repeated with a more concentrated sample. In the region of the curve between point A and point B, corresponding to concentrations A' and B', the maximum rate of precipitation is a convenient function of the concentration, and this is the preferred range for an analytical sample. In the region of the curve between point B through point C and extending to point D, the maximum rate of precipitation again changes somewhat slowly with concentration, and samples falling in this range are discarded as out of range high and the reaction is repeated with a more dilute sample. In the region of the curve between point D and point E, the maximum rate of precipitation is equivalent to that for a sample in the region of the curve between A and B. However, in such samples, the amount of antigen is in excess of the equivalent amount. Antigen excess samples must be distinguished from those which are in the antibody excess region of the curve, and the reaction must be repeated at an appropriately greater dilution. In the region of the curve corresponding to antigen concentrations greater than point E, the sample may be described as being in extreme antigen excess. The maximum rates of precipitation observed for samples in this region of the curve are the same as those for samples containing very little antigen, i.e. concentrations less than point A. Hence, extreme antigen excess samples must also be identified and repeated at an appropriate dilution. The method of the invention described in more detail below provides a procedure for identifying which samples are in antigen excess.

Figure 3:
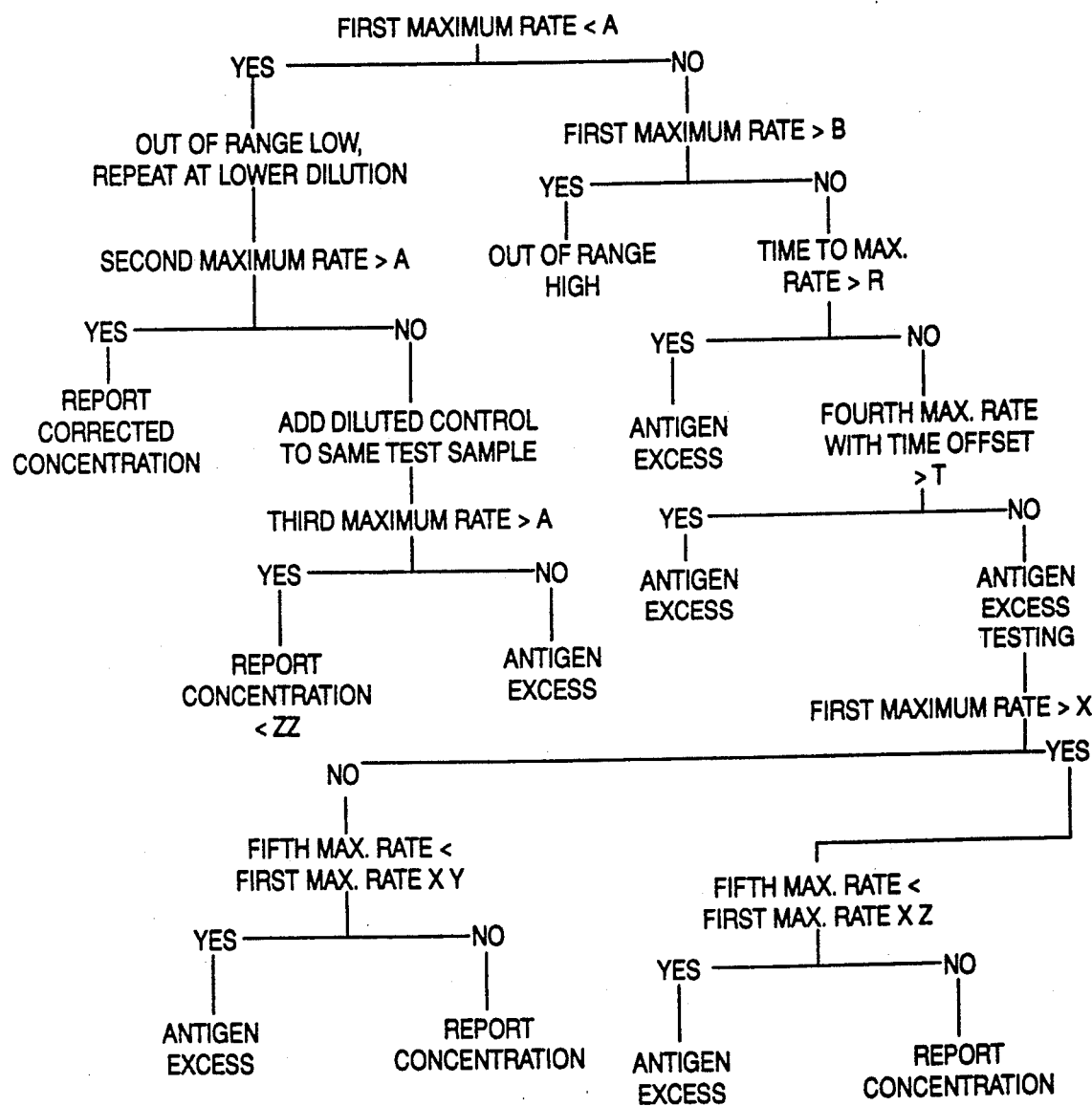
FIG. 3 shows a flowchart for the method of this invention.

The procedure is outlined in the chart of FIG. 3. After each test step of the method, a decision is made in accordance with the information supplied by the test. Some test results permit the immediate determination of a condition of antigen excess or of a reportable result. Other results lead to further testing.

Once the reference curve for the particular precipitin reaction to be used has been generated, an analytical sample is prepared by appropriate dilution of a physiological sample obtained from a patient. For example, in analysis of blood serum proteins, the physiological sample is comprised of a blood serum sample taken from a patient. The sample is diluted to provide an analytical sample having a target concentration falling within the A-B range of the reference curve. This initial dilution is calculated based on the usual physiological concentrations of the analyte, e.g. IgA, IgG, IgM, and the like.

The analytical sample is then mixed with the same predetermined amount of antibody used in the preparation of the reference curve, and the precipitin reaction is followed by observing the light scattered from the sample in a conventional nephelometer. The intensity of the scattered light is recorded at a number of times after the initiation of the reaction during an interval extending until the precipitation is substantially complete or for a predetermined time. The data so obtained are then fitted to the curve defined by equation (2), and the maximum rate of precipitation is calculated as described above. The method then proceeds as follows:

Step 1—Maximum rate less than A

If the calculated maximum rate for the test observation sample is less than A, the sample is considered to be too dilute for accurate measurement, and the method proceeds to Step 2. If the calculated maximum rate is greater than A, the method proceeds to Step 3.

Step 2—Testing for samples having maximum rate less than A

Step 2a—Out of range low testing

If a test sample has a maximum rate less than A in Step 1, a new sample is prepared by diluting the physiological sample so that the concentration of analyte is higher than in the first sample, and the precipitin reaction is repeated to determine a new maximum rate. If the new maximum rate is greater than A, the concentration of the physiological sample is calculated and reported, taking account of the greater dilution of the sample of Step 2a.

Step 2b—Testing for extreme antigen excess

If the maximum rate of the less dilute sample of Step 2a is still less than A, an aliquot of a control solution containing a defined amount of antigen is added, and the scattering produced by any further precipitation which may occur is recorded as above.

If the sample contains virtually no antigen, the reaction cuvette contains a relatively large amount of unreacted antibody which is available to react with the antigen present in the control solution. Thus, a maximum rate obtained following addition of the control solution will be in the A to B range and the sample will be considered as too dilute for accurate measurement. For certain commonly analyzed serum antigens, e.g. IgA, IgG, and IgM, the concentration is reported as being less than a defined value ZZ, which is tabulated in Table 1 below. Depending on the analyte being determined, such a sample may be regarded as indicating essentially no analyte in the physiological sample, or a still more concentrated sample may be prepared from the physiological sample and subjected to analysis.

If the sample is in the extreme antigen excess portion of the curve, virtually all of the antibody will have reacted with the antigen in the sample, and there will be no antibody remaining to react with the antigen in the added control solution. In this situation, the maximum rate of the precipitation reaction following the addition of the control solution will again be less than or equal to A, and the sample is considered as being in antigen excess.

Step 3—Maximum rate greater than B

If the maximum rate calculated in Step 1 is greater than A, it is compared to the maximum rate corresponding to point B, the high end of the calibrated range for the method. If the maximum rate is greater than B, the result is reported as too concentrated for accurate analysis. If the maximum rate is less than or equal to B, the method proceeds to Step 4.

Step 4—Time to maximum rate test

In certain situations of antigen excess, especially when the physiological sample is being analyzed for IgM, the reaction rates are extremely slow and are characterized by a long lag phase after the reaction is initiated during which little or no reaction occurs. As a result, the time required for the precipitin reaction to attain its maximum rate is much greater than would be expected for a sample not in antigen excess. Accordingly, the time to maximum rate is calculated by equation (4) and compared with a known value R which can be used to discriminate samples in clear antigen excess from those which need further testing. If the time to reach maximum rate exceeds R, the sample is considered to be in antigen excess. If the time to reach maximum rate does not exceed R, the method proceeds to Step 5. Values for R for certain common analytes are tabulated in Table 1 below.

Step 5—Maximum rate with time delayed reading

In some antigen excess situations, especially when the amount of IgA or IgM is to be determined, the precipitin reaction has a moderately long lag phase, and the reactions continue for a longer period than expected for a sample which is not in antigen excess. In order to provide a criterion for distinguishing this situation, the data recorded in the initial determination of maximum precipitation rate are modified by discarding all values recorded before a predetermined time S. A curve is fitted to the modified data according to the procedure described above, and the maximum rate of precipitation based on the modified data is calculated. If the maximum rate calculated using the modified data is greater than a predetermined value T, the sample is considered as being in antigen excess. If the maximum rate calculated using the modified data is not greater than T, the method continues to Step 6. Values of S and T for certain common analytes are tabulated in Table 1 below.

Step 6—Addition of second aliquot of physiological sample

Samples which are not determined to be in antigen excess in Step 4 or Step 5 remain as ambiguous results. In order to distinguish on which side of the reference curve these samples fall, a second aliquot of the physiological sample is added to the reaction mixture constituting the observation test sample. If the sample of Step 5 is in antibody excess (i.e. the antigen concentration is below the equivalence point C) the reaction mixture will contain unreacted antibody which is free to react with the antigen present in the second aliquot of physiological sample. This latter precipitin reaction will produce a secondary maximum rate. If, on the other hand, the sample is in antigen excess, very little unreacted antibody will remain in the test sample, and the addition of the second aliquot will produce little or no additional precipitin reaction.

The intensity of light scatter as a function of time is recorded for the precipitin reaction occurring after the addition of the second sample aliquot, the data is again fitted to a curve of the form of equation (2), and a new maximum rate is calculated. The maximum rate so obtained is compared to that calculated for the first sample. Due to the shape of the reference curve, two different comparisons can be made. If the maximum rate of the original test sample (first aliquot) was calculated to be less than the midpoint (or other point selected for analytical convenience) between A and B, a value indicated as X in Table 1 below, a maximum rate will be obtained following the addition of the second aliquot that is relatively high when compared to the initial maximum rate. If, on the other hand, the calculated maximum rate from the first aliquot was greater than the midpoint (or other point selected for analytical convenience) between A and B, the maximum rate calculated after adding the second aliquot of sample will not necessarily be high compared to the initial maximum rate due to the flattening of the reference curve as it approaches the equivalence point C.

Thus, once the second aliquot has been added and its maximum rate calculated, a decision is made. If the maximum rate of aliquot #1 is greater than the midpoint of the A-B range, the maximum rate of aliquot #2 must be greater than Z times the maximum rate of the first aliquot for the sample result to be reported as within the analytical range. The value of Z is indicated in Table 1 below. If the maximum rate of aliquot #2 is less than Z times the first maximum rate, the sample is reported as being in antigen excess. If the maximum rate of aliquot #1 is less than the midpoint of the A-B assay range, the maximum rate of aliquot #2 must be at least Y times the maximum rate of aliquot #1 for the sample result to be reported as within the calibrated assay range. If the maximum rate of aliquot #2 is less than Y times the maximum rate of aliquot #1, the sample is reported as being in antigen excess.

TABLE 1

|     | A   | B    | R   | S   | T   | X    | Y    | Z    | ZZ  |
|-----|-----|------|-----|-----|-----|------|------|------|-----|
| IgA | 60  | 600  | 500 | 220 | 30  | 330  | 0.5  | 0.3  | 8   |
| IgG | 300 | 3000 | 500 | 220 | 500 | 1650 | 0.45 | 0.15 | 100 |
| IgM | 40  | 400  | 250 | 220 | 10  | 240  | 0.3  | 0.3  | 8   |

The invention having now been fully described, it should be understood that it may be embodied in other specific forms or variations without departing from its spirit or essential characteristics. Accordingly, the embodiments described above are to be considered in all respects as illustrative and not restrictive, the scope of the invention being indicated by the appended claims rather than by the for(R)going description, and all changes which come within the meaning and range of equivalency of the claims are intended to be embraced therein.

I claim:

1. An immunochemical method for analyzing a bodily fluid comprising the steps of:
1) generating a reference curve by
   a) preparing a series of standard samples of fluid containing varied known amounts of an analyte, whereby each of said samples contains a known concentration of said analyte;
   b) initiating reaction of each of said standard samples with a predetermined amount of a complementary immunoreagent capable of forming an insoluble complex by reaction with said analyte to form a reaction mixture, whereby a precipitate of an immunocomplex begins to form in said reaction mixture and the formation of said precipitate continues over a period of time, whereby an increasing amount of said precipitate is present in said reaction mixture;
   c) for each of said reaction mixtures, detecting a physical property of said reaction mixture having a magnitude which is quantitatively proportional to the amount of said precipitate present in said reaction mixture and generating a signal having a numerical value proportional to the magnitude of said physical property;
   d) recording the value of said signal at a plurality of times within said period of time, whereby an assembly of data, comprising the numerical values of said signals and the times at which said values were recorded, is collected, said data representing the amount of said precipitate formed as a function of time;
   e) defining a mathematical function which represents the amount of said precipitate formed as a function of time in said reaction mixture, said function having the form $$S = \frac{M \times t^m}{(K + t^n)} + B$$

wherein S represents the amount of said precipitate, t represents time, m and n are constants between 1 and 3 preselected to provide an assumed precipitate versus time curve, and M, K and B are constants derived by fitting the data recorded in step 1) d) to said mathematical function;
   f) mathematically fitting the data recorded in step 1) d) to the function defined in step 1) e), whereby numerical values are determined for constants M, K and B and said constants in the function of step 1) e) are replaced by said numerical values;
   g) determining a maximum rate of formation of said precipitate for each reaction mixture by calculating a maximum rate of change of said function of step 1) e) from the constants M, K and B; and
   h) plotting said maximum rate of formation calculated in step 1) g) for each of said samples against the concentration of said analyte in said reaction mixture, whereby a reference curve is generated representing said maximum rate of formation of said precipitate which is characteristic of each concentration of said analyte, said reference curve having the property that said maximum rate of formation of precipitate
      has a maximum value defining an equivalence point for a concentration of said analyte approximately equivalent to said predetermined amount of complementary immunoreagent,
      has a value lower than said maximum value for a concentration of said analyte less than said equivalence point, and
      has a value lower than said maximum value for a concentration of analyte in excess of said equivalence point;
   i) defining a point A representing a concentration below said equivalence point on said reference curve which corresponds to a minimum concentration of said analyte to be reported from said reference curve;
   j) defining a point B representing a concentration below said equivalence point on said reference curve which corresponds to a maximum concentration of said analyte to be reported from said reference curve;
   k) defining a point X representing a concentration below said equivalence point on said reference curve between point A and point B;
2) initiating reaction of a fluid sample which is an aliquot of a body fluid sample containing an unknown quantity of said analyte with said predetermined amount of said complementary immunoreagent to form a test sample, whereby a precipitate of said immunocomplex begins to form in said test sample and the formation of said precipitate continues over a period of time;
3) calculating a maximum rate of formation of said precipitate formed in step 2) by
   a) detecting in said test sample said physical property of step 1) c) which is quantitatively proportional to the amount of said precipitate present in said reaction mixture at any time and generating a signal having a numerical value proportional to the magnitude of said physical property;

b) recording the values of said signal of step 3) a) at a plurality of times within said period of time of step 2), whereby an assembly of data, comprising the numerical values of said signal of step 3) a) and the times at which said values were recorded, is collected, said data representing the amount of said precipitate formed in step 2) as a function of time;

c) mathematically fitting the data recorded in step 3) b) to the function defined in step 1) e), whereby numerical values are determined for constants M, K and B and said constants in the function of step 1) e) are replaced by said numerical values;

d) determining a maximum rate of formation of said precipitate formed in step 2) by calculating a maximum rate of change of said function of step 1) e) from the constants M, K and B;

4) identifying the maximum rate of formation of said precipitate calculated in step 3) d) as a first maximum rate and if said first maximum rate is less than that associated with point A, rejecting said sample as too dilute for accurate measurement and repeating steps 2) and 3) using a less dilute fluid sample;

5) identifying the maximum rate of formation of said precipitate calculated in step 4) using said less dilute fluid sample as a second maximum rate, and if said second maximum rate is greater than that associated with point A, and less than that associated with point B, reading a concentration of said analyte from the reference curve at the point corresponding to said second calculated maximum rate of formation and reporting the concentration of said analyte in said test sample of step 4;

6) if said second maximum rate of formation is less than that associated with point A, adding to said test sample of step 4) a solution containing a predetermined amount of said analyte and again calculating a maximum rate of formation of precipitate of said immunocomplex by performing steps 3) a) through 3) d);

7) identifying said maximum rate of formation of said precipitate calculated in step 6) as a third maximum rate and if said third maximum rate is greater than that associated with point A, reporting said less dilute sample as containing a concentration of analyte which is less than the concentration associated with point A;

8) if said third maximum rate is less than that associated with point A, reporting said test sample as presenting a condition of antigen excess;

9) if said first maximum rate is greater than that associated with point A and greater than that associated with point B, reporting said test sample as containing an amount of analyte too great for accurate measurement;

10) if said first maximum rate of formation is greater than that associated with point A and less than that associated with point B, calculating a time interval between said reaction initiation of step 2) and the time said reaction reaches said first maximum rate;

11) if the time interval calculated in step 10) is greater than a predetermined interval;

reporting said test sample as presenting a condition of antigen excess;

12) if the time interval calculated in step 10) is less than said predetermined interval of step 11), determining a second precipitate versus time function from the data recorded in step 3) b) by again performing step 3) c) through step 3) d) using a value t−D in place of t, where D is a predetermined time, and all data points collected at less than time D are omitted from the curve fitting procedure, and calculating from said second precipitate versus time function a fourth maximum reaction rate;

13) if said fourth maximum reaction rate is greater than a predetermined value T, reporting said test sample as presenting a condition of antigen excess;

14) if said fourth maximum reaction rate is less than or equal to said predetermined value T, adding a second aliquot of said sample to said reaction and again performing steps 3) a) through 3) d) to calculate therefrom a fifth maximum reaction rate;

15) if said first maximum reaction rate is greater than that associated with point X and said first maximum reaction rate multiplied by a predetermined factor Z is less than or equal to said fifth maximum reaction rate, reporting said test sample as presenting a condition of antigen excess;

16) if said first maximum reaction rate is greater than that associated with point X and said first maximum reaction rate multiplied by a predetermined factor Z is greater than said fifth maximum reaction rate, reporting a concentration of analyte in the test sample by reading a value corresponding to the first maximum reaction rate from the reference curve between points A and B;

17) if said first maximum reaction rate is less than or equal to that associated with point X and said first maximum reaction rate multiplied by a predetermined factor Y is less than or equal to said fifth maximum reaction rate, reporting the test sample as presenting a condition of antigen excess;

18) if said first maximum reaction rate is less than or equal to that associated with point X and said first maximum reaction rate multiplied by a predetermined factor Y is greater than said fifth maximum reaction rate, reporting a concentration of analyte in the test sample by reading a value corresponding to said first maximum reaction rate from the reference curve between points A and B.

2. The method of claim 1 wherein m and n are each equal to 2.

3. The method of claim 1 wherein point X is the midpoint value of concentration between A and B.

4. The method of claim 1 wherein said physical property of said reaction mixture is light scattering.

* * * * *

UNITED STATES PATENT AND TRADEMARK OFFICE
CERTIFICATE OF CORRECTION

PATENT NO. : 5,019,999
DATED : May 28, 1991
INVENTOR(S) : Chester Swirski, Jr.

It is certified that error appears in the above—identified patent and that said Letters Patent is hereby corrected as shown below:

Column 16, line 31, delete "less than or equal to" and insert -- greater than --; line 38 delete "greater than" and insert -- less than or equal to --; line 46, delete "less than or equal to" and insert -- greater than --; line 53, delete "greater than" and insert -- less than or equal to --;

Signed and Sealed this

Fifth Day of January, 1993

Attest:

DOUGLAS B. COMER

Attesting Officer

Acting Commissioner of Patents and Trademarks